United States Patent [19]

Twerdochlib et al.

[11] Patent Number: 5,033,858
[45] Date of Patent: Jul. 23, 1991

[54] DETECTION OF CONTAMINANTS IN A LIQUID STREAM

[75] Inventors: Michael Twerdochlib, Oviedo; Richard B. G. Chianese, Altamonte Springs, both of Fla.

[73] Assignee: Westinghouse Electric Corp., Pittsburgh, Pa.

[21] Appl. No.: 485,009

[22] Filed: Feb. 26, 1990

[51] Int. Cl.$^5$ .............. G01N 21/85; G01N 15/02; G01N 15/14; G08B 21/00
[52] U.S. Cl. .................... 356/436; 356/335; 356/441; 340/621; 73/61 R
[58] Field of Search .............. 356/335, 336, 323, 341, 356/432, 411, 436, 441; 340/619, 620, 621; 73/655, 656, 657, 653, 590, 61 R

[56] References Cited

U.S. PATENT DOCUMENTS

| 3,915,570 | 10/1975 | Skala | 356/73 |
| 4,674,879 | 6/1987 | Gregorig et al. | 356/301 |
| 4,738,536 | 4/1988 | Kitamori et al. | 356/441 |
| 4,740,086 | 4/1988 | Oehler et al. | 356/432 |
| 4,783,599 | 11/1988 | Borden | 250/574 |
| 4,900,152 | 2/1990 | Wiegleb | 356/411 |

FOREIGN PATENT DOCUMENTS 974141 11/1982 U.S.S.R. .

Primary Examiner—Vincent P. McGraw
Assistant Examiner—LaCharles P. Keesee
Attorney, Agent, or Firm—K. Bach

[57] ABSTRACT

In a method and apparatus for detecting the presence of contaminants in a liquid stream which may also contain gas bubbles, the gas bubbles are detected by mechanically generating an alternating hydraulic pressure in the liquid stream, and monitoring the response of gas bubbles in the stream to the alternating hydraulic pressure.

24 Claims, 2 Drawing Sheets

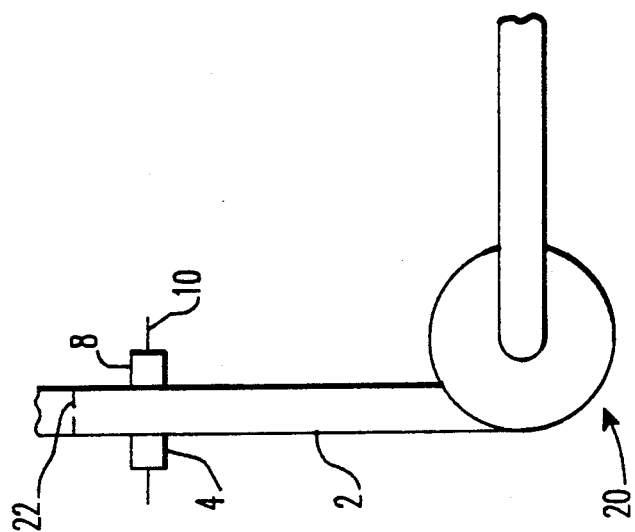
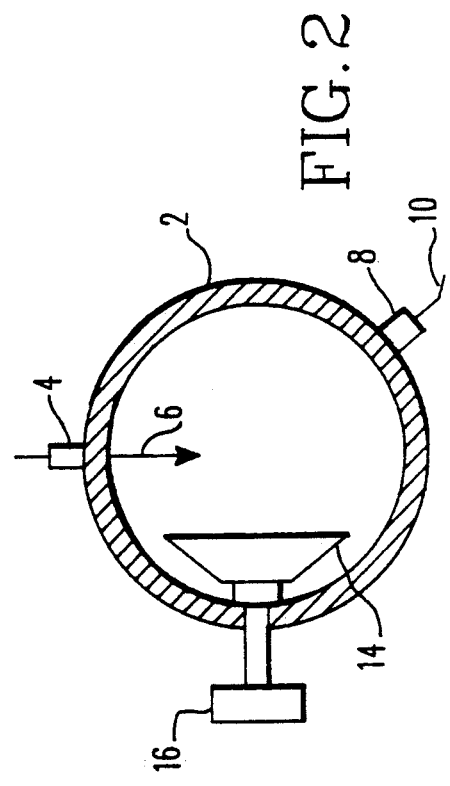
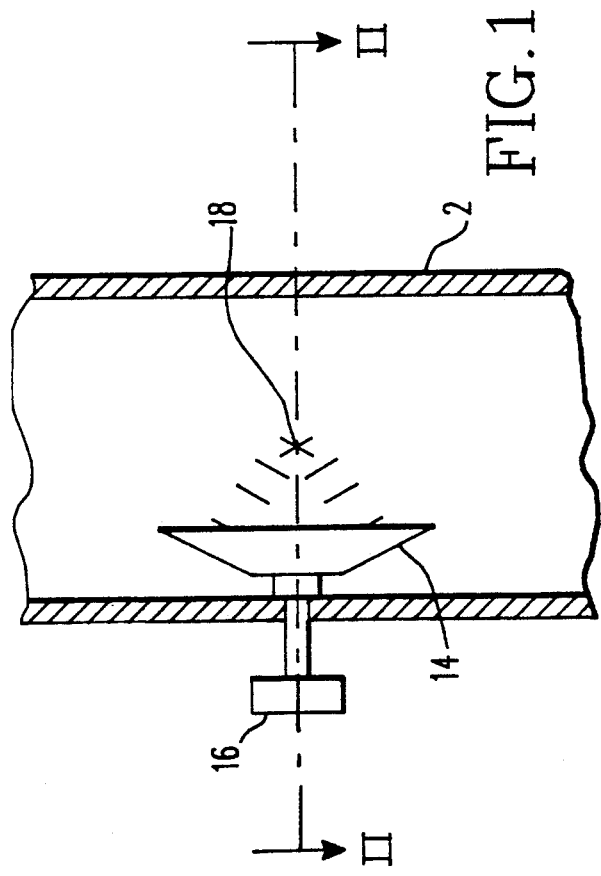

5,033,858

DETECTION OF CONTAMINANTS IN A LIQUID STREAM

BACKGROUND OF THE INVENTION

The present invention relates to methods and devices for detecting the presence of contaminants in a liquid stream, and is particularly concerned with preventing gas bubbles entrained in the stream from falsifying the detection result.

A number of techniques are known for monitoring liquids for various purposes. For example, in machinery equipped with a system for circulating oil which serves to lubricate bearings, it is advantageous to monitor the oil in order to detect and quantify metal particles which are present in the oil as a result of bearing wear. According to one known technique, the oil is caused to flow through a passage where the oil stream is traversed by a light beam which would be scattered by small metal particles in the oil stream. Any scattered light is detected and the detection result is processed to provide an indication of the presence and concentration of such small particles.

In monitoring systems of this type, it has been found that small air bubbles may also become entrained in the oil stream and can effect scattering of the light beam in a manner analogous to metal particles. This can produce a false indication of the presence of metal particles in the stream, possibly resulting in the generation of an alarm which will lead operating personnel to take inappropriate corrective actions.

It is also known to induce pressure pulsations in a liquid stream by directing a modulated light beam into the liquid so that impurities therein will produce heat that results in periodic thermal expansion of the liquid. Such an arrangement is disclosed in U.S. Pat. No. 4,738,536. An arrangement of this type will produce only a low level of pressure modulation and appears to require the presence of impurities in a sufficient concentration.

SUMMARY OF THE INVENTION

It is a primary object of the present invention to reliably prevent the presence of gas bubbles in a liquid stream from producing a false indication of the presence of solid particles therein.

A more specific object of the invention is to reliably detect the presence of small gas bubbles in a liquid stream in a manner which is distinguishable from the detection of solid particles in the stream.

Another object of the invention is to effect particle detection in a manner which removes the influence of gas bubbles from the detection result.

The above and other objects are achieved, according to the present invention, in a method and apparatus for detecting the presence of contaminants in a liquid stream which may also contain gas bubbles, by:
  mechanically generating an alternating hydraulic pressure in the liquid stream; and
  monitoring the response of gas bubbles in the stream to the alternating hydraulic pressure.

Mechanical generation of the alternating pressure within the liquid stream permits large amplitude pressure variations to be created, resulting in a substantial deformation of any bubbles present in the liquid stream. If the presence of bubbles is monitored by detecting the scattering of light by the bubbles, such substantial deformations will result in correspondingly large variations in the amplitude of the detected scattered due to the presence of bubbles

BRIEF DESCRIPTION OF THE DRAWING

FIG. 1 is a schematic cross-sectional view of a first embodiment of a system for implementing the present invention.

FIG. 2 is a cross-sectional view taken along the line II—II of FIG. 1.

FIG. 3 is a schematic cross-sectional view of a second embodiment of a system for implementing the present invention.

DESCRIPTION OF THE PREFERRED EMBODIMENTS

Figure 4:
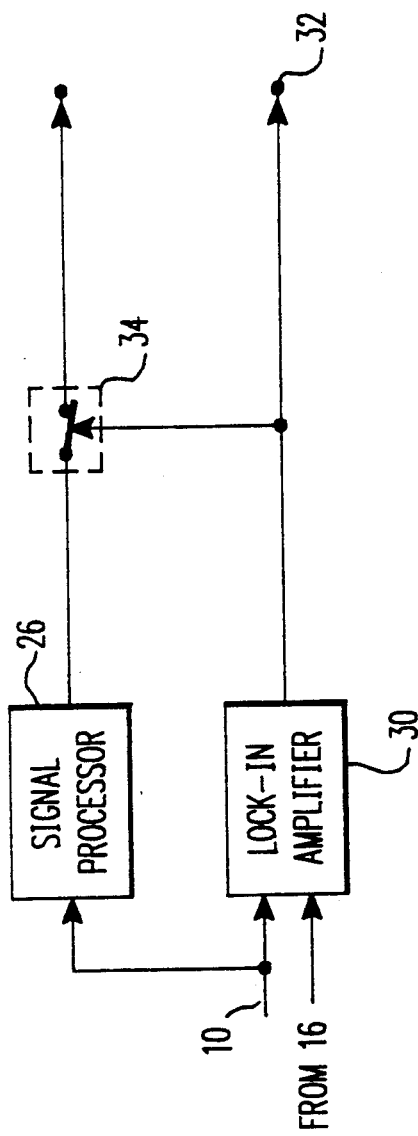
FIG. 4 is a block diagram of a first embodiment of a signal processing circuit used in the practice of the present invention.

Referring to FIGS. 1 and 2, there is shown a portion of a conduit 2, which may be a pipe or tube, for conducting a stream of lubricating oil or other liquid which is to be monitored for the presence of metal particles. To perform such monitoring, the wall of conduit 2 carries a light emitter 4 which emits a light beam having a defined width into the oil stream along a path 6. Any metal particles passing through the light beam act as scattering centers and light scattered in a given direction will impinge on a light detector 8 which supplies an electrical signal representative of the quantity of light received to an output lead 10. As is known in the art, detector 8 may be disposed in line with axis 6 or, as shown, may be laterally offset from axis 6.

The arrangement described thus far is known in the art and can be implemented with conventional devices.

Under various conditions, the oil stream conveyed along conduit 2 may also carry entrained air bubbles which will scatter light in a manner not detectably different from small metal particles.

In order to differentiate between such air bubbles and metal particles, conduit 2 is provided, according to the present invention, with an acoustic horn 14 immersed in the oil stream and driven by an electrical signal produced by a signal source 16 to produce an alternating pressure signal which acts on the oil stream in the region of light path 6. Preferably, acoustic horn 14 is of a type which focuses acoustic energy at a confined focal region 18 which preferably coincides with the axis of the light beam produced by emitter 4. The acoustic energy produced by horn 14, particularly at focal region 18, will cause the size of any entrained air bubbles to vary adiabatically in synchronism with the alternating acoustic energy, resulting in a corresponding modulation of the light scattering produced by those air bubbles. This acoustic energy will have a substantially smaller influence on the light scattering behavior of small metal particles since the size and shape of those particles will be substantially uninfluenced by the acoustic energy.

In order to enhance the modulation of the scattered light by small air bubbles, the frequency of the signal produced by source 16, and thus of the alternating acoustic energy produced by horn 14, is given a value substantially greater than the quotient of the velocity of the liquid stream through conduit 2 divided by the width of the light beam produced by emitter 4. As a result, each air bubble passing through the light beam will experience a plurality of pressure modulation cycles. Preferably, the relation between the flow velocity, the width of the light beam and the frequency of the alternating acoustic energy produced by horn 14 is selected to subject each bubble to at least 3 or 4 pressure modulation cycles. The number of pressure variation cycles can be selected on the basis of the characteristics, and particularly the response time, of the circuit provided for amplifying the detector output signal.

In the embodiment shown in FIG. 3, the oil stream is propelled through conduit 2 by a vane or piston pump 20 which inherently applies a pulsating propulsion force to the oil stream. Downstream of pump 20, conduit 2 is provided with a restriction 22 presenting an orifice dimensioned to cause the pulsating propulsion force produced by pump 20 to generate longitudinal pressure oscillations which will act on air bubbles entrained in the oil stream in a manner similar to horn 14. Light emitter 4 and light detector 8 are mounted on conduit 2 at a location spaced downstream from pump 20 by a distance sufficient to permit entrained air bubbles to stabilize after passing through pump 20. The structure and operating speed of pump 20 can be selected to assure that entrained air bubbles will influence the light beam during an appropriate number of pressure pulsation cycles.

Pump 20 may be driven by a drive-signal which bears a relation to the pressure oscillations produced in conduit 2 such that the drive signal can be processed to produce an alternating signal which is synchronized with the pressure pulsations This alternating signal may be used in signal processing circuitry to be described below.

Since the present invention generates a pressure oscillation or pulsations mechanically, the presence of air bubbles will result in the production of large amplitude modulations of the detected signal. Therefore, the circuitry provided for amplifying and processing the modulation components caused by air bubbles need not have a high level of sensitivity, and can thus be constructed to have a relatively short response time.

One embodiment of signal processing circuitry in accordance with the present invention is illustrated in FIG. 4 where the signal on output lead 10 is supplied both to a signal processor 26 of the type normally employed for producing indications of the presence of solid particles in the liquid stream and to one input of a lockin amplifier 30 which also receives, as a synchronous signal, a signal corresponding to the horn driving signal supplied by source 16 of FIGS. 1 and 2, or an alternating signal produced from the signal driving pump 20 of FIG. 3 as described above. Amplifier 30 produces a d.c. output signal representative of the component of the signal in lead 10 which corresponds in frequency to, and has a selected phase relative to, the signal supplied from source 16. Thus, the output signal from amplifier 30 will be representative of the degree of light scattering produced by air bubbles in the liquid stream. The output of amplifier 30 is connected to an output terminal 32 and to the control input of an electronic switch 34 so that when the output signal from amplifier 30 reaches or exceeds a selected amplitude, an alarm may be triggered by a device connected to terminal 32 and switch 34 may be opened to block transmission of the detection signal produced by processor 26.

While the arrangement illustrated in FIG. 4 has the advantage of a high degree of selectivity of signals produced by air bubbles and a high signal-to-noise ratio, the amplitude of the light scattering signals produced by air bubbles in an arrangement according to the invention will frequently be sufficient to allow the detection of air bubbles to be effected by means of a simple amplifier and bandpass filter tuned to the frequency of the signal produced by source 16. This arrangement is less expensive than systems of the type shown in FIGS. 4 and 5 and can be suitably used with the embodiment shown in FIG. 3 when a signal synchronized with the alternating pressure is not available.

Figure 5:
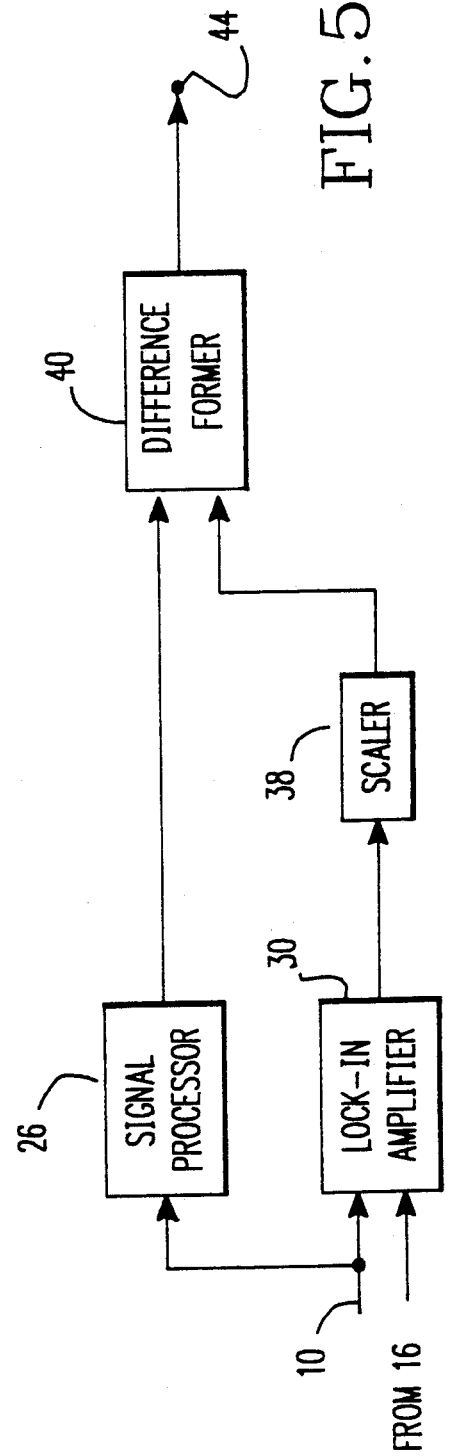
FIG. 5 is a block diagram of a second embodiment of such a circuit.

FIG. 5 illustrates a further arrangement according to the present invention in which the output signal component produced by air bubbles is employed to directly modify the output signal produced by signal processor 26 in order to directly provide a corrected output signal indicative of solid particles in the liquid stream. This circuit includes a scaler 38 connected to the output of amplifier 30 in order to adjust the output signal from amplifier 30 so that the scale of that signal is the same as that of the signal produced by processor 26. The signal produced by processor 26 will include a component due to light scattering from solid particles and a component due to light scattering from air bubbles. The scaling factor set by scaler 38 is selected, on the basis of calibration tests, so that the output signal from scaler 38 is equal to that component of the output signal from processor 26 which is the result of light scattering from air bubbles. Thus, by subtracting the signal from scaler 38 from that produced by signal processor 26, in a difference former 40, there is produced, at an output terminal 44, a corrected signal corresponding to that which would be produced by solid particles in the liquid stream in the absence of air bubbles.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. In a method for detecting the presence of contaminants in a liquid stream which may also contain gas bubbles, the improvement comprising:
    mechanically generating an alternating hydraulic pressure in the liquid stream; and
    monitoring the response of gas bubbles in the stream to the alternating hydraulic pressure.

2. A method as defined in claim 1 wherein said step of monitoring is carried out by directing a light beam at a location where the stream is subjected to the alternating pressure, and detecting light scattered in a given direction from the location.

3. A method as defined in claim 2 wherein the liquid stream is flowing in a given direction at a defined flow velocity, the light beam follows a path transverse to the given direction and has a defined transverse dimension parallel to the given direction, and the alternating pressure has a frequency which is substantially greater than the quotient of the defined flow velocity of the stream divided by the defined transverse dimension of the light beam.

4. A method as defined in claim 2 wherein said step of detecting is carried out by: producing a first signal representative of the light scattered in the given direction; producing a second signal representative of the alternating pressure; and synchronously detecting the first signal with respect to the second signal.

5. A method as defined in claim 2 wherein said step of mechanically generating comprises: disposing an electrically driven acoustic energy generator in communication with the liquid stream; and supplying an alternating drive signal to the generator for causing the generator to couple alternating acoustic energy into the liquid stream.

6. A method as defined in claim 5 wherein the acoustic energy generator is operative for focusing the acoustic energy at the location.

7. A method as defined in claim 2 wherein said step of mechanically generating comprises: applying a pulsating propulsion force to the stream for propelling the stream, and constraining the stream in a manner to cause the propulsion force to establish the alternating pressure within the stream.

8. A method as defined in claim 2 further comprising measuring light detected in said detecting step in order to obtain an indication of the presence of solid particles in the liquid stream.

9. A method as defined in claim 8 further comprising suppressing the indication of the presence of solid particles when said step of monitoring produces an indication of the presence of gas bubbles.

10. A method as defined in claim 8 wherein said step of measuring comprises: providing a first indication of the total light detected in said detecting step; providing a second indication of the portion of light detected in said detecting step as a result of scattering by gas bubbles; and subtracting said second indication from said first indication in order to produce the indication of the presence of solid particles in the liquid stream.

11. A method as defined in claim 1 wherein the alternating hydraulic pressure causes gas bubbles in the liquid stream to vary in size in synchronism with alternations of the hydraulic pressure, and said step of monitoring comprises monitoring variations in size of bubbles in the liquid stream.

12. A method as defined in claim 11, further comprising directing through the liquid stream radiation which can be scattered by gas bubbles, and wherein said step of monitoring comprises monitoring variations in scattering of the radiation due to variations in the size of gas bubbles.

13. In apparatus for detecting the presence of contaminants in a liquid stream which may also contain gas bubbles, the improvement comprising:
means for mechanically generating an alternating hydraulic pressure in the liquid stream; and
means connected for monitoring the response of gas bubbles in the stream to the alternating hydraulic pressure.

14. Apparatus as defined in claim 13 wherein said means for monitoring comprise means for directing a light beam at a location where the stream is subjected to the alternating pressure, and means disposed for detecting light scattered in a given direction from the location.

15. Apparatus as defined in claim 14 wherein the alternating pressure has a frequency which is substantially greater than the quotient of the flow velocity of the stream divided by the width of the light beam transverse to the stream flow direction.

16. Apparatus as defined in claim 14 wherein said means for detecting comprise: first means for producing a first signal representative of the light scattered in the given direction; second means for producing a second signal representative of the alternating pressure; and means connected to said first and second means for synchronously detecting the first signal with respect to the second signal.

17. Apparatus as defined in claim 14 wherein said means for mechanically generating comprises: an electrically driven acoustic energy generator disposed in communication with the liquid stream; and means connected for supplying an alternating drive signal to said generator for causing said generator to couple alternating acoustic energy into the liquid stream.

18. Apparatus as defined in claim 17 wherein said acoustic energy generator is operative for focusing the acoustic energy at the location.

19. Apparatus as defined in claim 14 wherein said means for mechanically generating comprises: propulsion means for applying a pulsating propulsion force to the stream for propelling the stream, and means for constraining the stream in a manner to cause the propulsion force to establish the alternating pressure within the stream.

20. Apparatus as defined in claim 14 further comprising means connected for measuring light detected by said detecting means in order to obtain an indication of the presence of solid particles in the liquid stream.

21. Apparatus as defined in claim 20 further comprising means connected for suppressing the indication of the presence of solid particles when said monitoring means produces an indication of the presence of gas bubbles.

22. Apparatus as defined in claim 20 wherein said means for measuring comprises: first circuit means for providing a first indication of the total light detected in said detecting step; second circuit means for providing a second indication of the portion of light detected in said detecting step as a result of scattering by gas bubbles; and third circuit means connected to said first and second circuit means for subtracting said second indication from said first indication in order to produce the indication of the presence of solid particles in the liquid stream.

23. Apparatus as defined in claim 13 wherein said means for mechanically generating are operative to cause gas bubbles in the liquid stream to vary in size in synchronism with alternations of the hydraulic pressure, and said means for monitoring comprise means for producing an output signal representative of variations in size of gas bubbles in the liquid stream.

24. Apparatus as defined in claim 23 further comprising means for directing through the liquid stream radiation which can be scattered by gas bubbles, and wherein said means for monitoring are responsive to variations in scattering of the radiation due to variations the size of gas bubbles.

* * * * *